US010788558B2

(12) United States Patent
Topgaard et al.

(10) Patent No.: US 10,788,558 B2
(45) Date of Patent: Sep. 29, 2020

(54) QUANTIFICATION OF THE RELATIVE AMOUNT OF WATER IN THE TISSUE MICROCAPILLARY NETWORK

(71) Applicant: CR Development AB, Lund (SE)

(72) Inventors: Daniel Topgaard, Lund (SE); Samo Lasic, Lund (SE)

(73) Assignee: CR Development AB, Lund (SE)

( * ) Notice: Subject to any disclaimer, the term of this patent is extended or adjusted under 35 U.S.C. 154(b) by 318 days.

(21) Appl. No.: 15/939,991

(22) Filed: Mar. 29, 2018

(65) Prior Publication Data

US 2018/0224514 A1 Aug. 9, 2018

Related U.S. Application Data

(63) Continuation of application No. 14/410,549, filed as application No. PCT/SE2013/050755 on Jun. 24, 2013, now Pat. No. 10,031,204.

(Continued)

(30) Foreign Application Priority Data

Jun. 29, 2012 (SE) ...................................... 1250736

(51) Int. Cl.
*A61B 5/055* (2006.01)
*G01R 33/563* (2006.01)
(Continued)

(52) U.S. Cl.
CPC ...... *G01R 33/56341* (2013.01); *A61B 5/0263* (2013.01); *A61B 5/055* (2013.01);
(Continued)

(58) Field of Classification Search
CPC ..... A61B 5/0263; A61B 5/055; A61B 5/7207; F04C 2270/041; G01R 33/543;
(Continued)

(56) References Cited

U.S. PATENT DOCUMENTS 6,380,739 B1 4/2002 Machida
7,336,072 B2 2/2008 Assmann et al.
(Continued)

FOREIGN PATENT DOCUMENTS

CN 1857156 A 11/2006
CN 101023878 A 8/2007
(Continued)

OTHER PUBLICATIONS

Caprihan, A et al., "Flow Measurements BY NMR" Physics Reports. 198. No. 4 (1990) pp. 195-235.
(Continued)

*Primary Examiner* — Mark D Remaly
(74) *Attorney, Agent, or Firm* — Harness, Dickey & Pierce, P.L.C.

(57) ABSTRACT

The present invention discloses a method for magnetic resonance (MR) imaging comprising acquiring at least two MR images with different motion-weighting originating from a RF and gradient pulse sequence causing signal attenuation from diffusion but not flow (flow-compensated data); acquiring at least two MR images with different motion-weighting originating from a RF and gradient pulse sequence causing signal attenuation from diffusion and flow (non-compensated data); performing a model fit to the flow-compensated and non-compensated data in which at least one of the adjustable parameters are constrained to be the same for both sets of data; and obtaining quantitative information on microscopic flow by extracting at least one parameter of the intravoxel incoherent motion (IVIM) effect from the model fit, said method being directed to diffusion-perfusion.

14 Claims, 6 Drawing Sheets

Related U.S. Application Data

(60) Provisional application No. 61/665,998, filed on Jun. 29, 2012.

(51) Int. Cl.
    *A61B 5/00*         (2006.01)
    *A61B 5/026*      (2006.01)
    *G01R 33/565*     (2006.01)
    *G01R 33/54*      (2006.01)
    *G01R 33/56*      (2006.01)

(52) U.S. Cl.
CPC ........ *A61B 5/7207* (2013.01); *G01R 33/5635* (2013.01); *G01R 33/56366* (2013.01); *G01R 33/56509* (2013.01); *F04C 2270/041* (2013.01); *G01R 33/543* (2013.01); *G01R 33/5608* (2013.01)

(58) Field of Classification Search
CPC .......... G01R 33/5608; G01R 33/56341; G01R 33/5635; G01R 33/56366; G01R 33/56509
See application file for complete search history.

(56) References Cited

U.S. PATENT DOCUMENTS

| | | |
|---|---|---|
| 7,411,394 B2 | 8/2008 | Huang |
| 8,005,530 B2 | 8/2011 | Prince |
| 8,497,680 B2 | 7/2013 | Bieri et al. |
| 2004/0189297 A1 | 9/2004 | Bock et al. |
| 2006/0241389 A1 | 10/2006 | Assmann et al. |
| 2006/0261808 A1 | 11/2006 | Huang |
| 2010/0174175 A1 | 7/2010 | Prince |
| 2011/0044524 A1 | 2/2011 | Wang et al. |
| 2012/0242334 A1 | 9/2012 | Bieri et al. |
| 2013/0018252 A1 | 1/2013 | Irarrazaval |

FOREIGN PATENT DOCUMENTS

| | | |
|---|---|---|
| JP | 531099 H | 2/1993 |
| JP | 5123312 B2 | 5/1993 |
| JP | 10-75938 | 3/1998 |
| JP | 2008119514 A | 5/2008 |
| JP | 4357934 B2 | 11/2009 |
| WO | WO-200138895 A1 | 5/2001 |
| WO | WO-2006011810 A2 | 2/2006 |
| WO | WO-2007046172 A1 | 4/2007 |
| WO | WO-2009134820 A2 | 11/2009 |
| WO | WO-2013025487 A1 | 2/2013 |

OTHER PUBLICATIONS

Duerk, J.L et al., "In-Plane Flow Veloicty Quantification Along the Phase Encoding Axis in MRI" Magnetic Resonance Imaging. vol. 6. (1988) pp. 321-333.
International Search Report PCT/ISA/210 for International Application No. PCT/SE2013/050755 dated Nov. 14, 2013.
Le Bihan, Denis et al. "Separation of Diffusion and Perfusion in Intravoxel Incoherent Motion MR Imaging." *Radiology* 168 (1988): 497-505.
Sigmund, E.E. et al. "Intravoxel Incoherent Motion Imaging of Tumor Microenvironment in Locally Advanced Breast Cancer." *Magnetic Resonance in Medicine* 65 (2011): 1437-1447.
Luciani, Alain et al. "Liver Cirrhosis: Intravoxel Incoherent Motion MR Imaging—Pilot Study." *Radiology* 249 (2008): 891-899.
Lemke, Andreas et al. "An in Vivo Verification of the Intravoxel Incoherent Motion Effect in Diffusion-Weighted Imaging of the Abdomen." *Magnetic Resonsance in Medicine* 64 (2010): 1580-1585.
Provencher, Stephen W. "A Constrained Regularization Method for Inverting Data Represented by Linear Algebraic or Integral Equations." *Computer Physics Communications* 27 (1982): 213-227.
Le Bihan, D. et al. "Separation of Diffusion and Perfusion in Intravoxel Incoherent Motion MR Imaging." *Radiology* 168 (1988): 497-505.
Ahn, C.B. et al. "The effects of random direction distributed flow in nuclear magnetic resonance imaging." *Medical Physics* 14 (1987): 43-48.
Maki, Jeffrey H. et al. "The Use of Gradient Flow Compensation to Separate Diffusion and Microcirculatory Flow in MRI." *Magnetic Resonance in Medicine* 17 (1991): 95-107.
Callaghan, P.T. et al. "Spatial Coherence Phenomena Arising from Translational Spin Motion in Gradient Spin Echo Experiments." *Magnetic Resonance* 11.4 (1999): 181-202.
Wang, Zhiheng et al. "Measurement of Tumor Vascular Volume and MEan Microvascular Random Flow Velocity Magnitude by Dynamic Gd-DTPA-Albumin Enhanced and Diffusion-Weighted MRI." *Magnetic Resonance in Medicine* 40 (1998): 397-404.
Le Bihan, Denis and Robert Turner. "The Capillary Network: A link between IVIM and Classical Perfusion." *Magnetic Resonance in Medicine* 27 (1992): 171-178.
Kim, Tae and Seong-Gi Kim. "Quantification of Cerebral Arterial Blood Volume Using Arterial Spin Labeling With Intravoxel Incoherent Motion-Sensitive Gradients." *Magnetic Resonance in Medicine* 55 (2006): 1047-1057.
Hunter, M.W. et al. "PGSE NMR measurement of the non-local dispersion tensor for flow in porous media." *Journal of Magnetic Resonance* 204 (2010): 11-20.
Le Bihan, Denis et al. "Imaging of Diffusion and Microcirculation with Gradient Sensitization: Design, Strategy, and Significance." *Journal of Magnetic Resonance Imaging* 1 (1991): 7-28.
Le Behin, Denis et al. "Imaging of Diffusion and Microcirculation with Gradient Sensitization: Design, Strategy, and Significance." *Journal of Magnetic Resonance Imaging* 1 (1991): 7-28.
Alper, Joseph S. and Robert I. Gelb. "Standard Errors and Confidence Intervals in Nonlinear Regression: Comparison of Monte Carlo and Parametric Statistics." *Journal of Physical Chemistry* 949 (1990): 4747-4751.
van Kampen, NG. *Stochastic Processes in Physics and Chemistry*. North Holland, Amsterdam, 1981. 10-11, 44-46, 52-89, 128-133, 405-407.
Extended European Search Report dated Jan. 2, 2017 issued in corresponding European Application No. 13810505.1.
Westscherek, Andreas et al. "Flow compensated IVIM as a tool to probe microvasculature." *Proceedings of the International Society for Magnetic Resonance in Medicine* 20 (2012): 2012.
Westscherek, A. et al. "Investigation of the theoretical background of the IVIM model using flow compensated DWI." *Proceedings of the International Society for Magnetic Resonance in Medicine* 19 (2011): 2011.
Kim, Sungheon et al. "Interstitial fluid pressure correlates with initravoxel incoherent motion imaging metrics in a mouse mammary carcinoma model." *NMR in Biomedicine* 25 (2012): 787-794.
Mulkern, Robert et al. "Complimentary aspects of diffusion imaging and fMRI: II. Elucidating contributions to the fMRI signal with diffusion sensitization." *Magnetic Resonance Imaging* 25 (2007): 939-952.
Fujita, N. et al. "Separation of Diffusion and Slow Flow Effects by Use of Flow Rephasing and Dephasing." *Magnetic Resonance in Medicine* 24 (1992): 109-122.
Callaghan, Paul T. and Yang Xia. "Velocity and Diffusion Imaging in Dynamic NMR Microscopy." *Journal of Magnetic Resonance* 91 (1991): 326-352.
Axel, Leon and Daniel Morton. "MR Flow Imaging by Velocity-Compensated/Uncompensated Difference Images." *Journal of Computer Assisted Tomography* 11:1 (1987): 31-34.
Japanese Office Action dated Mar. 28, 2017 issued in corresponding Japanese Application No. 2015-520119 (with translation).
Japanese Office Action dated Dec. 1, 2015 issued in corresponding Japanese Application No. 201380033778.6.

QUANTIFICATION OF THE RELATIVE AMOUNT OF WATER IN THE TISSUE MICROCAPILLARY NETWORK

CROSS-REFERENCE TO RELATED APPLICATIONS

This application is a continuation of U.S. application Ser. No. 14/410,549, filed on Dec. 22, 2014, which is a national phase under 35 U.S.C. § 371 of PCT International Application No. PCT/SE2013/050755 which has an International filing date of Jun. 24, 2013, which claims priority to Swedish patent application number SE 1250736-4, filed on Jun. 29, 2012 and benefit to U.S. patent application 61/665,998, filed on Jun. 29, 2012; the entire contents of each of which are hereby incorporated by reference.

BACKGROUND OF THE INVENTION

The present invention relates to a method for analyzing diffusion-weighted magnetic resonance (MR) images recorded with a variable amount of velocity compensation to quantify the amount and velocity of blood flowing in the tissue microvasculature.

Both molecular diffusion and perfusion, i.e., blood flowing in the orientationally disordered capillary network, lead to attenuation of the signal intensity in diffusion-weighted MR imaging, an effect known as "intravoxel incoherent motion" (IVIM). Pioneered by the work of Le Bihan (1), the pseudo-diffusion coefficient D* of the flowing water, the perfusion fraction f, and the diffusion coefficient D of the non-flowing extra- and intracellular water are estimated by biexponential analysis of diffusion-weighted MR images recorded as a function of the diffusion-weighting variable b. Such an analysis has recently been applied to breast cancer (2) and liver cirrhosis (3), indicating that the perfusion parameters (D* and f) could be useful for diagnosing pathological conditions in which the blood flow in the microvasculature is altered. The values of f range from 4% in brain to 25% in the pancreas (4). The analysis is hampered by the well-known problem of extracting exponential components with similar decay constants from noisy multi-exponential signal attenuation data (5). In order to obtain sufficient difference between D, which is independent of the diffusion time, and D*, which is approximately proportional to the diffusion time, diffusion-weighting is often performed at long echo times, e.g. 100 ms, thus leading to additional signal reduction and influence of noise due to nuclear spin-spin relaxation.

The signal attenuation originating from perfusion can partially be removed by employing diffusion-weighting gradient modulation schemes in which the phase shifts of spins flowing at a constant velocity are refocused (6-8). Images obtained by taking the difference of flow-compensated and non-compensated images yield information on capillary density (6, 7). Unfortunately, the image signal-to-noise ratio (SNR) is usually too low to accurately quantify pathologically induced changes of intravascular fractions using analysis methods based on difference images.

The inordinate sensitivity to noise of currently existing protocols for signal acquisition and analysis (biexponential fit to signal vs. b data or difference images of flow-compensated and non-compensated data) have so far prevented a widespread clinical use of the potentially informative perfusion parameters. Based on the considerations above, it would be desirable to have the means for obtaining these parameters with greater accuracy and less sensitivity to noise than possible with currently existing methods.

U.S. Pat. No. 7,336,072 a method for visualizing macroscopic flow in MRI is presented. The method provides analysis of data obtained by the flow compensated and non-compensated sequence. The information about macroscopic flow (velocity) is contained in the phase of the signal and it is extracted by the method disclosed in U.S. Pat. No. 7,336,072. Based on the signal phase information, the velocity filed is constructed to visualize macroscopic flow. Different visualization methods are presented in U.S. Pat. No. 7,336,072, e.g. using color coded maps or vector fields. For comprehensive flow image data reading, the velocity field is superimposed on an anatomical image. To identify regions with flow and stationary tissue, the magnitudes of the signals acquired by flow compensated and non-compensated sequences are subtracted.

SUMMARY OF THE INVENTION

The invention relates to a data analysis method and corresponding image acquisition protocol overcoming the previously mentioned problems. The present invention enables the effects of diffusion and perfusion on the pseudo-diffusion coefficient to be analyzed separately based on the data from experiments with variable degree of flow compensation. Varying the degree of flow compensation allows for a more robust quantification of dispersed flow.

According to a one aspect of the present invention there is provided a method for magnetic resonance (MR) imaging comprising:
acquiring at least two MR images with different motion-weighting originating from a RF and gradient pulse sequence causing signal attenuation from diffusion but not flow (flow-compensated data);
acquiring at least two MR images with different motion-weighting originating from a RF and gradient pulse sequence causing signal attenuation from diffusion and flow (non-compensated data);
performing a model fit to the flow-compensated and non-compensated data in which at least one of the adjustable parameters are constrained to be the same for both sets of data; and obtaining quantitative information on microscopic flow by extracting at least one parameter of the intravoxel incoherent motion (IVIM) effect from the model fit.

It should be mentioned that the extraction of the at least one parameter of course may be related to extracting several parameters of the intravoxel incoherent motion (IVIM) effect. Moreover, according to one specific embodiment the extraction is related to extracting the information about the fraction of the microcapillary water and the velocity dispersion or the pseudo-diffusion value, which are attributed to the intravoxel incoherent motion (IVIM), from the model fitted data set.

The method according to the present invention, when being compared to that disclosed in U.S. Pat. No. 7,336,072, is also based on the analysis of the data acquired by flow compensated and non-compensated sequences. However, the analysis method aims to quantify the intravoxel incoherent motion effect (IVIM effect). The aim of the method according to the present invention is to quantify the relative amount water in tissue micro-capillary network with higher precision and accuracy compared to the established approaches, i.e. bi-exponential and segmented fit of the attenuation data. The present method also allows for a quantification of the velocity dispersion within the microcapillary network. In contrast, the method disclosed in U.S.

Pat. No. 7,336,072 aims at quantification of velocity in macroscopic flow. Furthermore, the analysis according to the present invention is based on the signal magnitude data, while the macroscopic velocity filed extracted by the method in U.S. Pat. No. 7,336,072 is based on the signal phase data. The method according to the present invention is based on a constrained fit of the flow compensated and non-compensated data. No such data fitting method is presented in U.S. Pat. No. 7,336,072. As notable from above, the method according to the present invention, as disclosed in the present claim 1, is very different from the method disclosed in U.S. Pat. No. 7,336,072.

As said above, according to the present invention, the effects of diffusion and perfusion on the pseudo-diffusion coefficient can be analyzed separately based on the data from experiments with variable degree of flow compensation. As a special case, data from flow-compensated and non-compensated experiments is considered. The inventors suggest a novel diffusion-perfusion experiment with variable degree of flow compensation and a novel joint analysis of the flow compensated and non-compensated data to quantify flow with improved accuracy and precision compared to the conventional methods.

Information about the probability distribution $P(D,v_d^2)$ can be obtained by regressing the equation (18) below onto the signal attenuation data $E(b,\alpha)$ at variable b and $\alpha$.

Pulse sequences that allow for independent adjustment of diffusion weighting, b, and velocity dispersion weighting, $\alpha$, can be used to quantify the velocity dispersion by disentangling the diffusion and the velocity dispersion contributions to the total signal attenuation, characterized by the pseudo-diffusion coefficient, D*. In the diffusion-perfusion correlation experiment (D-P), where the experimental parameters b and $\alpha$ can be adjusted independently, the measurement of the correlation between the diffusion coefficient and the velocity dispersion allows associating the velocity dispersion components and the corresponding diffusion components when one or more diffusion or velocity dispersion components are present in the system.

Joint bi-exponential analysis of signal attenuation data acquired with both flow-compensated and non-compensated gradient modulation schemes yields estimates of the root-mean-square flow velocity v and the fractional population f of water flowing in the microcapillary network, as well as the diffusion coefficient D of the "stationary" water in the surrounding tissue. The flow-compensated and non-compensated schemes are optimized for yielding maximum insensitivity and sensitivity to flow, respectively, for given constraints on hardware performance and nuclear relaxation times.

Further specific embodiments of the present invention are presented below and in the claims. The present invention has many possible application areas. For instance, the obtained quantitative information on microscopic flow may be used for diagnosing disease. Possible uses are as a method for diagnosing tumor vascular properties, such as blood volume fraction and/or microvascular flow velocity, e.g. by use of the parameters CBV (cerebral blood volume) and/or CBF (cerebral blood flow). Examples of indications to diagnose are breast cancer or liver cirrhosis.

DETAILED DESCRIPTION OF THE INVENTION

Figure 1:
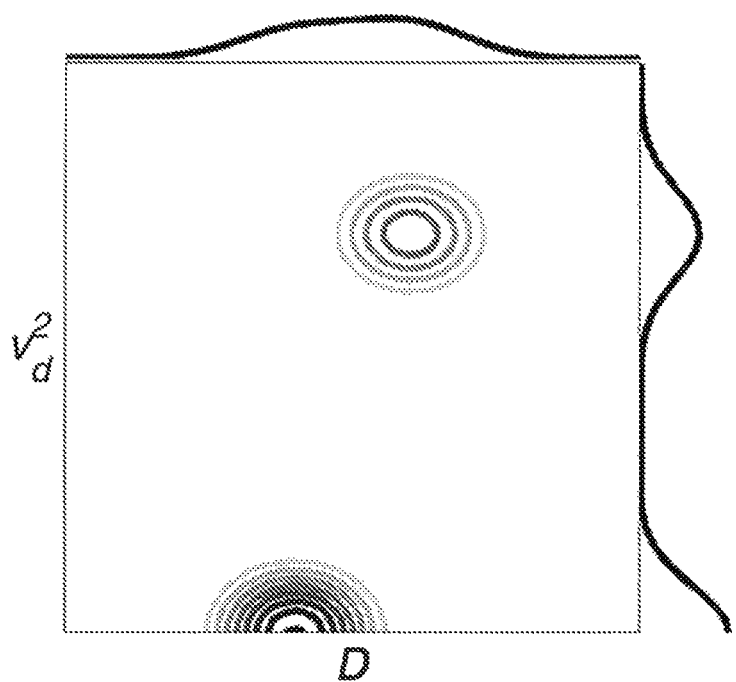
FIG. 1 displays a schematic representation of the probability distribution $P(D, v_d^2)$ for the example with two signal contributions described by Eq. (19) (see below).

Perfusion of blood in tissue is a significant physiological parameter. Vascular blood volume and flow velocity are well established as indicative parameters in tumor diagnosis and therapy. Despite a lot of effort, non-invasive methods for probing perfusion are very slowly paving their ground against clinically valuable but invasive methods like MRI methods based on paramagnetic contrast agents or methods which, for example, make use of radioactive tracers (9). The non-invasive diffusion based methods are very promising but have so far not proven adequate in routine clinical practice due to their inordinate sensitivity to noise. It has been shown that the effects of randomly oriented flow contribute to the signal attenuation in ordinary diffusion experiments (6-8). Consequently, the effects of random flow can be observed as superimposed on the molecular diffusion effects, resulting in bi-exponential signal attenuation (1). This effect, known as the "intravoxel incoherent motion" (IVIM) is quantified in terms of the perfusion fraction, f, and the so called pseudo-diffusion coefficient, D*.

Conventional perfusion measurements, based on the uptake or washout of radioactive tracers, provide information about the cerebral blood flow (CBF) and cerebral blood volume (CBV). The perfusion fraction, f, due to the IVIM effect, is proportional to the CBV parameter, while the product f D* is proportional to the CBF parameter (10). The exact relations between CBF/CBV and the IVIM parameters, viz. f and D*, depend on tissue and microcirculation properties. Likewise, the parameters obtained by the new analysis protocol, according to the present invention, are closely related to CBV and CBF. It has been shown that in vivo evaluation of CBV and CBF parameters is possible also with the diffusion-weighted arterial spin labeling MRI technique based on the IVIM analysis (10, 11). With reference to the above described, the method according to the present invention may be directed to evaluating tumor systems. Therefore, according to one specific embodiment of the present invention, the quantitative information is related to tumor vascular properties, such as blood volume fraction and/or microvascular flow velocity, e.g. consisting of at least parameters CBV (cerebral blood volume) and/or CBF (cerebral blood flow).

In flow-compensated NMR diffusion experiments, on the other hand, the additional attenuation due to perfusion can be avoided, potentially allowing for the effects of flow and diffusion to be separated (7). A combination of the flow compensated and non-compensated PGSE NMR technique can be used to extract information about the non-local dispersion tensor, representing a fundamental description of dispersive flow in terms of temporal and spatial correlations (12). Although in tissue the pseudo-diffusion coefficient is an order of magnitude larger than the regular diffusion coefficient, the perfusion contributes only a small fraction (about 10%) to the observable signal, thus it is very hard to reliably detect. Analysis of the IVIM effect in diffusion weighted MRI, accounting for relaxation effects, indicates that perfusion fraction in pancreas is about 25% while only about 4% in brain. Monte Carlo error analysis shows that large signal-to-noise ratios are required for accurate estimation of the perfusion fraction (13). Despite this limitation, diffusion based detection of perfusion is tempting, since it allows non-invasively separating the contributions of blood flow and capillary volume in different physiologic and pathologic conditions.

In terms of temporal displacement correlations, two extreme cases of dynamics can be identified, i.e. the non-correlated diffusive motion and the coherent flow. Due to spatial variation of resonance frequency in inhomogeneous magnetic fields, the observable NMR signal carries information about mean properties of motion on the time-scale of the NMR experiment. In a spin-echo experiment, the echo attenuation is proportional to diffusion coefficient while the signal phase is proportional to the mean flow velocity. Flow compensated NMR diffusion experiments are designed to eliminate the phase shift due to flow. In some cases the dynamic properties of several sub-ensembles of nuclei affect the NMR signal. Such case may result, for example, if nuclei with different diffusive properties are probed, e.g. due to different molecular species or when nuclei remain isolated in morphologically different environments within the probed sample volume during the NMR experiment. The two component diffusion due to extracellular and intracellular water in tissue is a well-known example of the latter case. The dispersed flow, in which several sub-ensembles of nuclei with constant but diverse velocities coexist, is yet another example of several sub-ensemble contributions. Even though the velocities of these contributions may be constant on the experimental time-scale, their phase contributions would be incoherent due to velocity dispersion, bringing about an additional attenuation factor in experiments without flow compensation. This is known as the IVIM model, which describes the bi-exponential spin echo attenuation in terms of diffusivity of stationary tissue without perfusion and as an additional attenuation due to flow (perfusion) quantified as the pseudo-diffusion coefficient D*. The effects of diffusion and perfusion on the pseudo-diffusion coefficient can be analyzed separately based on the data from experiments with variable degree of flow compensation. Varying the degree of flow compensation allows for a more robust quantification of dispersed flow. As a special case, data from flow-compensated and non-compensated experiments is considered. The inventors suggest a novel diffusion-perfusion experiment (D-P experiment) with variable degree of flow compensation and a novel joint analysis of the flow compensated and non-compensated data to quantify flow with improved accuracy and precision compared to the conventional methods.

In an ideally homogeneous magnetic field, the spin phase is coherent and the magnetization is revolving with the Larmor frequency $\omega_0 = \gamma B_0$, where $\gamma$ is the nuclear gyromagnetic ratio and $B_0$ is the magnetic field strength. In the rotating frame, defined by the mean magnetic field $B_0$, the observable NMR signal is given by spin ensemble average $$S(t) = S_0 \langle e^{-j\varphi(t)} \rangle, \quad (1)$$

where $S_0$ is the signal magnitude after excitation, comprising the effects of relaxation and initial spin distribution, and $\varphi$ is the relative phase of individual spin contributions given by the varying magnetic field gradient G(t) and the relative spin displacement z(t) along the gradient as $$\varphi(t) = -\gamma \int_0^t G(t')z(t')dt'. \quad (2)$$

Note that displacements and velocities are related by $$z(t) = \int_0^t v(t')dt'. \quad (3)$$

The phase can be expressed with velocity, by introducing the dephasing factor q(t), as $$q(t) = \gamma \int_0^t G(t')dt', \quad (4)$$

which vanishes at the time of spin-echo, t i.e. $q(t_E)=0$.
At the time of spin-echo, $t_E$, the relative phase from Eq. 2 is thus given by $$\varphi(t_E) = \int_0^{t_E} q(t)v(t)dt. \quad (5)$$

The ensemble average of the exponent in Eq. 1 can be expressed as an exponent of averages in terms of cumulant series (14). In the Gaussian approximation, i.e. neglecting cumulant contributions of order higher than two, the observable signal at the time of spin-echo, $t_E$, is given by $$S(t_E) = \sum_k S_k e^{-i\phi_k(t_E) - \beta_k(t_E)}, \quad (6)$$

where the summation runs over all the sub-ensemble contributions with different weights $S_k$, cumulative phase $\phi_k$ and attenuation $\beta_k$ factors. Note that possible sub-ensemble differences in relaxation times are accounted for in the $S_k$ coefficients. The cumulative phase is proportional to the sub-ensemble mean velocity, $$\phi_k(t_E) = \langle v_k \rangle \alpha, \quad (7)$$

with $$\alpha = \gamma \int_0^{t_E} G(t')t'dt' = -\int_0^{t_E} q(t')dt'. \quad (8)$$

Note that for flow-compensated sequences $\alpha=0$. The attenuation, on the other hand, is given by velocity fluctuations $u_k = v_k - \langle v_k \rangle$ and expressed in terms of the velocity autocorrelation function (VACF), $\langle u_k(t_1)u_k(t_2) \rangle$, as $$\beta_k = \frac{1}{2}\int_0^{t_E} dt_1 \int_0^{t_E} dt_2 q(t_1)\langle u_k(t_1)u_k(t_2)\rangle q(t_2). \quad (9)$$

Note that for non-correlated velocity fluctuations the VACF can be approximated as a Dirac delta function with diffusion coefficient $D_k$ as $$\langle u_k(t_1)u_k(t_2)\rangle = 2D_k\delta(t_2-t_1), \quad (10)$$

yielding the attenuation $$\beta_k = D_k \int_0^{t_E} q(t)^2 dt = D_k b, \quad (11)$$

where b is the diffusion weighting factor.

In case of flow dispersion, the averaging over sub-ensembles in Eq. 6 with different velocities gives rise to an additional attenuation term. The extent of phase coherence loss due to dispersed flow, leading to additional signal attenuation, depends on the observation time relative to flow velocity and to the characteristic length-scale, l, on which flow velocity changes take place. If flow velocity varies during the experimental time, e.g. due to variation in flow direction relative to the position/motion encoding gradients, the phase coherence is lost, leading to diffusion-like signal attenuation. The apparent diffusion coefficient due to flow with velocity v can in such case be approximated as $D_v = lv/6$ (1). A presence of a net flow will however yield a cumulative phase shift when $\alpha > 0$. Here we consider another extreme case, which assumes that different sub-ensembles have constant but different velocities during the experimental time. This corresponds to a capillary network model consisting of straight segments which are long enough so that the blood flow does not change direction during the experimental time (see FIG. 3b in Ref. 1).

For a set of sub-ensembles with common diffusion coefficient, D, the Eq. 6 can be written as $$S(t_E) = e^{-bD}\sum_k S_k e^{-i\alpha\langle v_k\rangle} = S_0 e^{-bD}\int_{-\infty}^{\infty} P_v e^{-i\alpha v}dv, \quad (12)$$

where P(v) is the velocity probability density. The function P(v) can account for different velocity dispersion models corresponding to flow in tissue (1, 6). If for simplicity, a Gaussian distribution with the width $\langle v_2\rangle$ is assumed, $$P_v = \frac{1}{\sqrt{2\pi\langle v^2\rangle}}e^{-\frac{v^2}{2\langle v^2\rangle}}, \quad (13)$$

the Eq. 12 results in $$S(t_E) = S_0 e^{-bD}e^{-\frac{1}{2}\alpha^2\langle v^2\rangle}. \quad (14)$$

The total attenuation factor in Eq. 14 is often expressed in terms of pseudo-diffusion coefficient, D*, $$S(t_E) = S_0 e^{-bD^*}. \quad (15)$$

Comparison of Eqs. (14) and (15) gives the pseudo-diffusion coefficient as $$D^* = D + \frac{\alpha^2}{b}v_d^2. \quad (16)$$

Note that the ratio $\alpha^2/b$ depends on the gradient pulse sequence design. To maximize the effect of flow, manifested in the pseudo diffusion coefficient, the pulse sequence can be designed to maximize the ratio $\alpha^2/b$. In Eq. 16, we introduce $v_d^2$ as a measure of velocity dispersion, which scales with velocity depending on a particular velocity dispersion model. If a Gaussian velocity distribution is assumed, according to Eq. 13 and the subsequent Eq. 14, $v_d^2$ is given by $$v_d^2 = \frac{\langle v^2\rangle}{2}. \quad (17)$$

Note that the scaling factor in Eq. 17, reflecting the relation of $v_d^2$ to the actual microscopic properties of flow, can be complex and it is irrelevant to the analysis according to the present invention. If for example, straight capillary segments with plug flow and an even angular distribution are assumed, the resulting echo-attenuation is given by a sinc function of plug flow velocity (6), which in the Gaussian approximation gives the scaling factor of ⅙, instead of ½ (see Eq. 17) and $\langle v^2\rangle$ representing the square of the plug flow velocity. The Eq. (14) describes the case with a single D and $\langle v^2\rangle$ contribution. When more diffusion or velocity dispersion components are present in the system, Eq. (14) can be generalized as the Laplace transform of the probability distribution $P(D, v_d^2)$, where the experimental parameters b and $\alpha^2$ are reciprocal to the system parameters D and $v_d^2$. For a multi-component system, the normalized signal attenuation is given by $$E(b,\alpha) = \frac{S(b,\alpha)}{S_0} = \int_0^\infty\int_0^\infty P(D, v_d^2)e^{-bD}e^{-\alpha^2 v_d^2}dDdv_d^2. \quad (18)$$

The probability distribution is normalized, so that $$\int_0^\infty\int_0^\infty P(D, v_d^2)dDdv_d^2 = 1.$$

The $P(D, v_d^2)$ is given by the inverse Laplace transform of the measured signal intensity $E(b,\alpha)$. The correlation between different diffusion components (D) and the velocity dispersion components ($v_d^2$) can be revealed by the $P(D, v_d^2)$. Information about the probability distribution $P(D,v_d^2)$ can be obtained by regressing the equation (18) onto the signal attenuation data $E(b,\alpha)$ at variable b and $\alpha$.

Pulse sequences that allow for independent adjustment of diffusion weighting, b, and velocity dispersion weighting, $\alpha$, can be used to quantify the velocity dispersion by disentangling the diffusion and the velocity dispersion contributions to the total signal attenuation, characterized by the pseudo-diffusion coefficient, D*. In the diffusion-perfusion correlation experiment (D-P), where the experimental parameters b and $\alpha$ can be adjusted independently, the measurement of the correlation between the diffusion coefficient and the velocity dispersion allows associating the velocity dispersion components and the corresponding diffusion components when one or more diffusion or velocity dispersion components are present in the system.

Different signal contributions might exist in tissue, some affected by both perfusion and diffusion, some affected only by diffusion. For example, one may consider two signal contributions; one for which the attenuation is given by both the diffusion coefficient, $D_f$, and the velocity dispersion $v_d^2$, and another, for which the attenuation is given only by the diffusion coefficient D. The normalized signal intensity is in this case given by $$E(b,\alpha) = f e^{-bD_f} e^{-\alpha^2 v_d^2} + (1-f) e^{-bD}. \quad (19)$$

Here f is the fraction of the contribution with perfusion. The probability distribution $P(D, v_d^2)$ for the example summarized by the Eq. 19 is schematically illustrated in FIG. 1. Note that the two contributions, represented as peaks at the $(D_f, v_d^2)$ and $(D,0)$ coordinates on the $P(D, v_d^2)$ contour plot, can only be resolved along the $v_d^2$ axis, which is reciprocal to $\alpha^2$. Thus varying α at different diffusion weighting b provides a means of resolving the velocity dispersion components and thus correlating the velocity dispersion components and the diffusion components. If the system can be described by two diffusion components and one velocity dispersion component, the diffusion coefficients D and $D_f$, the velocity dispersion $v_d^2$ and the ratio f can be quantified by regressing the equation (19) onto the signal attenuation data.

Several pulse sequences meet the criterion of allowing for independent variation of α and b to achieve the D-P experiment. While different gradient modulation schemes can be used, including different oscillating gradient waveforms, the examples shown in FIGS. 2 and 3 make use of pulsed gradients.

Figure 2:
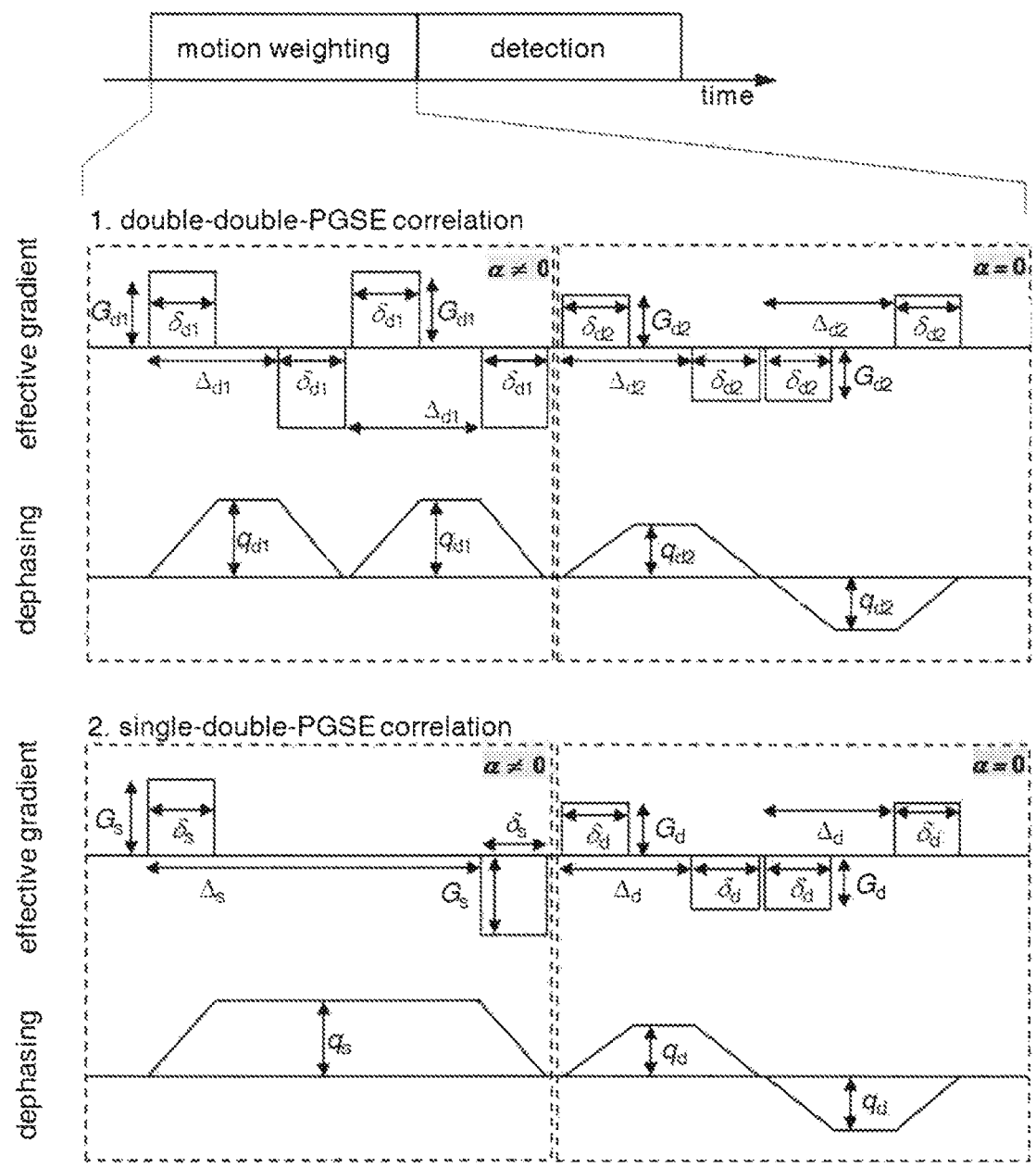
FIG. 2 displays schematics of pulse sequences for motion weighted nuclear magnetic resonance (NMR) or magnetic resonance imaging (MRI).

The examples of the D-P pulse sequences shown in FIG. 2 can be view as consisting of two consecutive motion sensitizing blocks, from which one is flow compensated (α=0) and the other is not flow compensated. In FIG. 2.1, the D-P sequence consists of two different double-PGSE blocks, each with its own gradient amplitudes, $G_{d1}$ and $G_{d2}$ and timing parameters, $\delta_{d1}, \delta_{d2}, \delta_{d1}, \delta_{d2}$. The first block is not flow compensated, the second block is flow compensated (α=0). α and b can be independently adjusted by varying two of the gradient amplitudes $G_{d1}$, $G_{d2}$ and/or durations $\delta_{d1}, \delta_{d2}$ and/or pulse separations $\Delta_{d1}, \Delta_{d2}$. The D-P sequence in FIG. 2.2 consists of a single PGSE block and a double-PGSE block, each with its own gradient amplitudes, $G_s$ and $G_d$ and timing parameters, $\delta_s, \delta_d, \delta_s, \delta_d$. The first block is not flow compensated, the second block is flow compensated (α=0). α and b can be independently adjusted by varying two of the gradient amplitudes $G_s$, $G_d$ and/or durations $\delta_s, \delta_d$ and/or pulse separations $\Delta_s, \Delta_d$. A special case of this example is when the gradient pulse duration is identical for all the pulses, $\delta=\delta_s=\delta_d$. In that case, the dephasing magnitude is given by $q_{s,d}=\gamma G_{s,d}\delta$, the velocity dispersion weighting $\alpha=q_s\Delta_s$ and the diffusion weighting $$b = q_s^2 \left(\Delta_s - \frac{\delta}{3}\right) + 2q_d^2 \left(\Delta_d - \frac{\delta}{3}\right).$$

α and b can be adjusted independently by adjusting $q_s$ and $q_d$.

Figure 3:
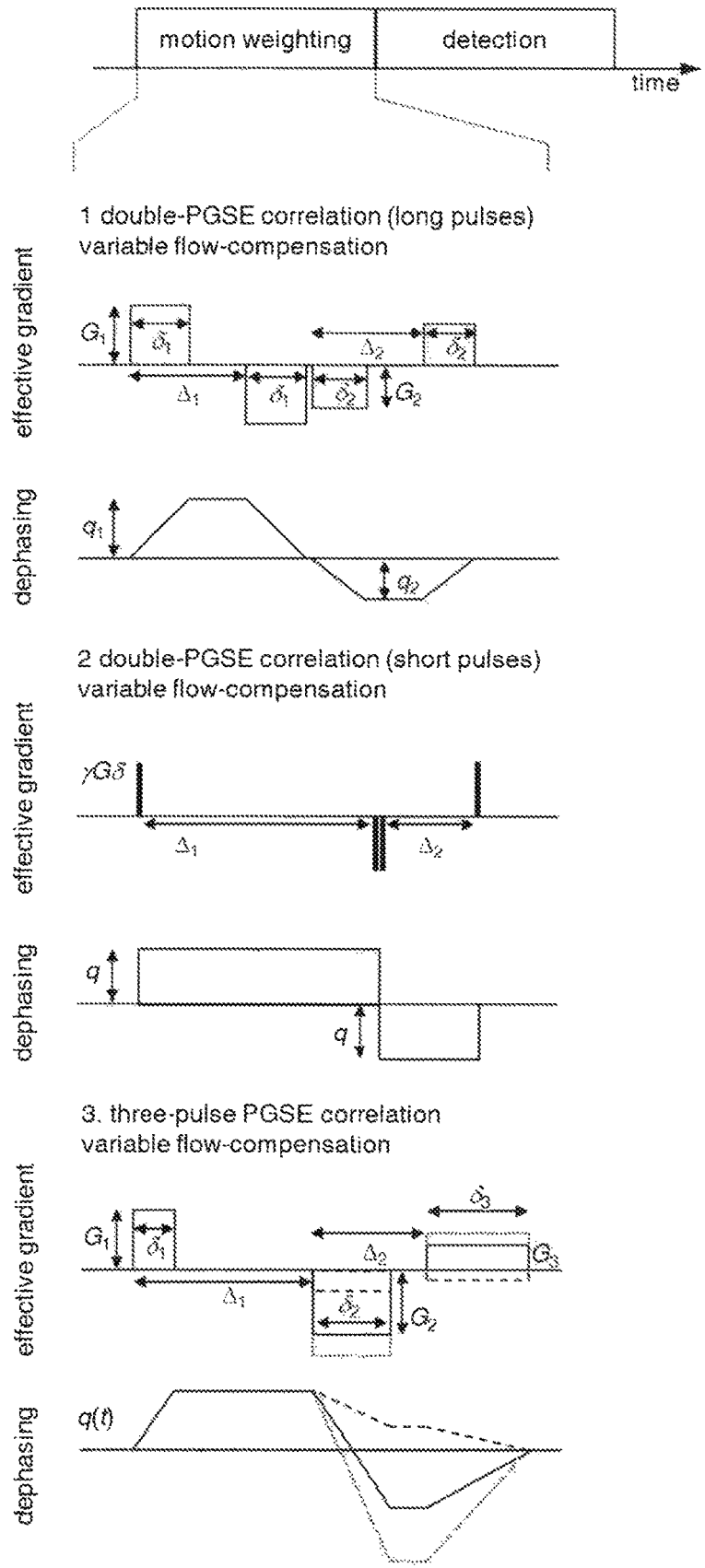
FIG. 3 also displays schematics of pulse sequences for motion weighted nuclear magnetic resonance (NMR) or magnetic resonance imaging (MRI).

The examples shown in FIG. 3 can be viewed as a single block design where α and b can be adjusted independently. The D-P sequence in FIG. 3.1 consists of two single PGSE blocks, each with its own gradient amplitudes, $G_1$ and $G_2$ and timing parameters, $\delta_1, \delta_2, \Delta_1, \Delta_2$. The entire block allows for variable flow compensation (α). α and b can be independently adjusted by varying two of the gradient amplitudes $G_1$, $G_2$ and/or durations $\delta_1, \delta_2$ and/or pulse separations $\Delta_1, \Delta_2$. A special case of this example is when the gradient pulse durations are identical for all the pulses, $\delta=\delta_1=\delta_2$, and pulse separations are identical in the two PGSE blocks, $\Delta=\Delta_1=\Delta_2$, so that the dephasing magnitude is given by $q_{1,2}=G_{1,2}\delta$, velocity dispersion weighting by $\alpha=(q_1-q_2)\Delta$ and the diffusion weighting by $$b = (q_1^2 + q_2^2)\left(\Delta - \frac{\delta}{3}\right).$$

α and b can be adjusted independently by adjusting $q_1$ and $q_2$. Yet another special case of the example shown in FIG. 3.1 is the example shown in FIG. 3.2. In this example, the gradient pulse durations are short, $\delta=\delta_1=\delta_2\rightarrow 0$, and gradient magnitudes are all identical, $|G_1|=|G_2|=G$, so that the dephasing magnitude is given by $q=\gamma G\delta$, and the pulse separations are varied so that their sum is a constant diffusion time, $t_d=\Delta_1+\Delta_2$, and the difference, expressed as $\varepsilon=\Delta_1-\Delta_2$, can span the interval $0-t_d$. The velocity dispersion weighting is then given by $\alpha=q\varepsilon$ and the diffusion weighting by $b=q^2 t_d$. α and b can be adjusted independently by adjusting q and ε. In the D-P sequence example shown in FIG. 3.3, the gradient modulation consists of three gradient pulses with amplitudes $G_1$, $G_2$ and $G_3$ and timing parameters $\delta_1, \delta_2, \delta_3, \Delta_1, \Delta_2$. The entire block allows for variable flow compensation (α). The echo condition $$q(t_E) = \int_0^{t_E} G(t')dt' = 0$$

constrains the relations between the three gradient pulse amplitudes $G_1$, $G_2$ and $G_2$ and durations $\delta_1, \delta_2, \delta_3$. α and b can be independently adjusted by varying two of the gradient amplitudes $G_1$, $G_2$ and $G_3$ and/or durations $\delta_1, \delta_2, \delta_3$ and/or pulse separations $\Delta_1, \Delta_2$. A special case for this gradient modulation example is when the gradient pulse durations are identical for the three pulses, $\delta=\delta_1=\delta_2=\delta_3$, and pulse separations are identical, $\Delta=\Delta_1=\Delta_2$. In this case, the gradient amplitudes are related by $G_2=-(G_1+G_3)$, the dephasing magnitude is given by $q_{1,3}=\gamma G_{1,3}\delta$, the velocity dispersion weighting by $$\alpha = \frac{1}{2}(q_1 - q_3)\Delta$$

and the diffusion weighting by $$b = \frac{1}{6}(q_1^2 + q_3^2)(3\Delta - 2\delta) - \frac{1}{3}q_1 q_3 \delta.$$

α and b can be adjusted independently by adjusting $q_1$ and $q_3$.

For implementation of the D-P experiment on a clinical scanner, the sequences 3.1 and 3.3 might be best suited since they can be conveniently implemented in combination with the different read out protocols. These sequences, particularly the one shown in FIG. 3.3, may, with an appropriate choice of sequence timing parameters, require minimum gradient switching and are thus favored by the gradient slew rate and amplitude limitations often encountered in clinical scanners.

The experiment may be performed also by using only two values of the parameter α, where one value set to zero and the other value is set to a value different from zero. Such experiment can be performed in two parts, by using a flow compensated sequence ($\alpha=0$) and by using a non-compensated sequence. Several pulse sequences may be used as a flow compensated sequence or non-compensated sequence. Some examples of such sequences are given in the FIG. 4.

For a single pulsed gradient spin-echo (single-PGSE) sequence with a pair of narrow pulses with intensity $G_s$ of duration $\delta_s$ and the separation between the leading edges of the pulses $\Delta_s$ (see FIG. 4.1), the dephasing magnitude is given by $$q_s = \gamma G_s \delta_s \qquad (20)$$

and the diffusion and velocity weighting factors are given by $$b = q_s^2 (\Delta_s - \delta_s/3) \qquad (21)$$

and $$\alpha = -q_s \Delta_s. \qquad (22)$$

The pseudo-diffusion coefficient (see Eq. 16) is given by $$D^* = D + \frac{\Delta_s^2}{\Delta_s - \delta_s/3} v_d^2. \qquad (23)$$

While D is independent of $\Delta$ in case of free diffusion and inversely proportional to $\Delta$ for restricted diffusion, D* is roughly proportional to $\Delta$ due to the dominant effect of flow (see Eq. 23). Note that Eq. 23 implies that the echo attenuation due to flow can be maximized by using long pulse separation times, such that $\Delta_s \gg \delta_s$.

Figure 4:
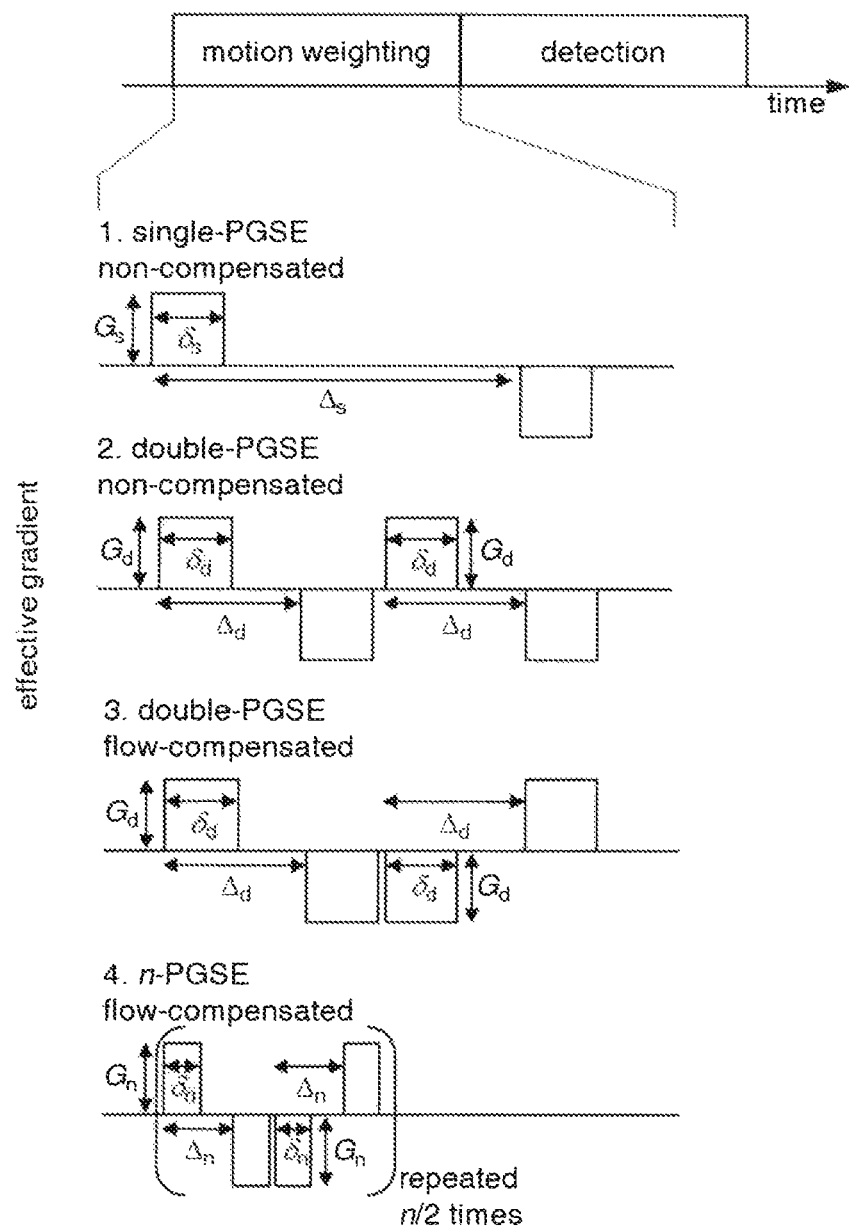
FIG. 4 shows commonly known pulse sequences for motion weighted nuclear magnetic resonance (NMR) or magnetic resonance imaging (MRI).

Flow compensation can be achieved with any oscillating gradient sequence, for which the condition $\alpha=0$ is true. Such sequences may employ harmonically oscillating gradients or any kind of gradient waveforms, which achieve diffusion weighting and flow compensation simultaneously. The flow compensated double-PGSE sequence (FIG. 4.3) or a repeated flow compensated double PGSE, denoted n-PGSE in FIG. 4.4, where n=2, 4, 6 . . . is an even integer corresponding to the number of gradient pulse pairs in the sequence, is just an example of the flow-compensated sequence we use in this description. In the case of n-PGSE sequence, the diffusion weighting is given by $$b_n = n q_n^2 (\Delta_n - \delta_n/3), \qquad (24)$$

where $q_n$, $\Delta_n$ and $\delta_n$ denote the corresponding parameters for a double-PGSE sequence (see FIG. 4.4).

For equal diffusion weighting b in a single-PGSE and in an n-PGSE experiment, the condition $$q_n = q_s \sqrt{\frac{(\Delta_s - \delta_s/3)}{n(\Delta_n - \delta_n/3)}} \qquad (25)$$

must be fulfilled. If in addition the dephasing magnitudes and the pulse durations are chosen to be identical for the single-PGSE and for the n-PGSE, setting $q_n=q_s$ and $\delta_n=\delta_s$ in condition (25) implies $$\Delta_n = \frac{\Delta_s}{n} + \delta_s/3 \left(1 - \frac{1}{n}\right). \qquad (26)$$

Along the lines of Eq. 6, the above description of signal attenuation (Eq. 14) could be expanded to include flowing and non-flowing populations with different diffusion coefficients. Here we consider a bi-modal attenuation, resulting from a flowing and a non-flowing population, assuming that molecular exchange between the two populations is negligible during experimental time. We denote f as the perfusion fraction, and 1−f as the diffusion fraction. The spin-echo intensity is in this case given by $$I_s(q_s, \Delta_s, \delta_s) = I_{0s} \left[ (1-f) e^{-q_s^2(\Delta_s - \delta_s/3)D} + f e^{-q_s^2(\Delta_s - \delta_s/3)D_f} e^{-q_s^2 \Delta_s^2 v_d^2} \right] \qquad (27)$$

and $$I_n(q_n, \Delta_n, \delta_n) = I_{0n} \left[ (1-f) e^{-n q_n^2 (\Delta_n - \delta_n/3)D} + f e^{-n q_n^2 (\Delta_n - \delta_n/3)D_f} \right] \qquad (28)$$

for the non-compensated single-PGSE and for the flow-compensated n-PGSE, respectively. Note that if D and $D_f$ are identical, the flow-compensated intensity Eq. 28 is described by a mono-exponential decay.

The analysis, according to the invention, does not relate to any particular diffusion weighting or flow-compensation gradient sequence. Analysis of the non-compensated and flow-compensated data sets may require adjustment to how the timing parameters, diffusion weighting and dephasing factors are calculated in Eqs. 27 and 28.

Figure 5:
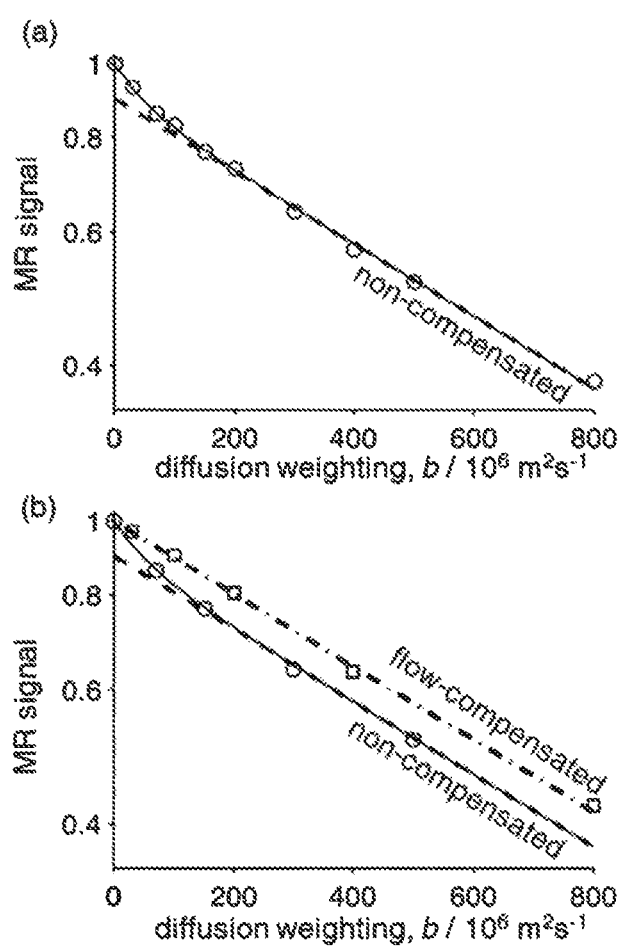
FIG. 5 shows simulated data for flow compensated and non-compensated pulse sequences.

Extraction of the D* or $v_d^2$ and f from the bi-exponential regression of Eq. 27 to the flow non-compensated (IVIM) dataset suffers from an inordinate sensitivity to noise. The flow compensated dataset provides additional information, by disentangling the effects of flow from the effects of diffusion. Here we suggest the simultaneous analysis of both flow-compensated and non-compensated datasets, which significantly improves the accuracy and precision of the estimated parameters of interest. By constraining the parameters D, $D_f$, and f to be identical for both the flow compensated and non-compensated datasets, the sensitivity to noise of the estimated parameters is considerably reduced compared to the standard analysis of IVIM dataset. FIG. 5 shows a comparison of accuracy and precision of the flowing fraction f estimates for the conventional protocols ("standard" and "segmented") and according to the present invention. The analysis is applied to simulated data based on experimentally extracted parameters by Sigmund et al. (2).

The Monte Carlo error estimation was used in prooving the efficiency of the present invention. Random noise is added to simulated data, which is then regressed with different protocols to obtain the fit parameters. This procedure is repeated 1000 times for each signal-to-noise level to obtain mean values and error estimates for the fit parameters (15). To ensure a fair comparison of the different analysis protocols, the same amount of data points is used in the conventional as in the new protocol. In the new protocol, only the data points corresponding to every second (even) b-value from the original series of b-values (used in the conventional protocols) are used in the flow-compensated dataset and only data points at the odd b-values from the original series are used in the non-compensated dataset (compare FIG. 5a and FIG. 5b). In FIG. 6a one can see that the "standard" analysis results in an overestimated f values and the "segmented" analysis results in an underestimated f values, while the new protocol yields considerably improved accuracy in the entire range of noise levels. As shown in FIG. 6b, the "segmented" protocol only slightly improves the precision over the "standard" protocol, while the new protocol yields significantly more precise estimates of f values over the entire range of noise levels.

DETAILED DESCRIPTION OF THE DRAWINGS

FIG. 1 displays a schematic representation of the probability distribution P(D, $v_d^2$) for the example with two signal contributions described by Eq. (19). The P(D, $v_d^2$) is given by the inverse Laplace transform of the measured signal E(b,α). The relation between E(b,α) and P(D, $v_d^2$) is given by Eq. (18). The contour lines connect points with equal probability density. The solid lines on top and on the right hand side of the contour plot represent the projections of the probability density function, i.e. the probability distribution of diffusion coefficients, D, and the probability distribution of velocity dispersions, $v_d^2$, respectively. On the contour plot of the P(D, $v_d^2$), two contributions are identified as peaks at ($D_f$, $v_d^2$) and (D,0). The two contributions cannot be resolved along the D-axis, which is reciprocal to the diffusion weighting b, while they can be resolved along the $v_d^2$-axis, which is reciprocal to $α^2$.

FIG. 2 displays schematics of pulse sequences for motion weighted nuclear magnetic resonance (NMR) or magnetic resonance imaging (MRI). The magnification of the motion encoding block shows the effective gradient wave form and the dephasing for two examples of the diffusion-perfusion correlation experiment, which can be viewed as composed of two motion encoding blocks, where the diffusion weighting, b, and the velocity dispersion weighting, a, can be adjusted independently: 1. double-double PGSE, the first double-PGSE is non-compensated (signal attenuation from diffusion and perfusion) and the second double-PGSE is flow-compensated (α=0, signal attenuation from diffusion but NOT from perfusion); 2. single-double PGSE, the first single-PGSE is non-compensated (signal attenuation from diffusion and perfusion) and the second double-PGSE is flow-compensated (α=0, signal attenuation from diffusion but NOT from perfusion).

FIG. 3 displays schematics of pulse sequences for motion weighted nuclear magnetic resonance (NMR) or magnetic resonance imaging (MRI). The magnification of the motion encoding block shows the effective gradient wave form and the dephasing for three examples of the diffusion-perfusion correlation experiment, which can be viewed as composed of one motion encoding block, where the diffusion weighting, b, and the velocity dispersion weighting, a, can be adjusted independently: 1. double-PGSE with long gradient pulses, where the independent timing parameters $δ_1$, $δ_2$, $Δ_1$, $Δ_2$ and the gradient magnitudes $G_1$ and $G_2$ allow for independent adjustment of the diffusion weighting, b, and the velocity dispersion weighting, α; 2. double-PGSE with short gradient pulses, where the independent timing parameters $Δ_1$, $Δ_2$ and the dephasing magnitude q allow for independent adjustment of the diffusion weighting, b, and the velocity dispersion weighting, α; 3. three-pulse PGSE, where the independent timing parameters $δ_1$, $δ_2$, $δ_3$, $Δ_1$, $Δ_2$ and the gradient magnitudes $G_1$ and $G_2$ are constraint by the echo condition (at the end of the motion encoding the dephasing is equal to zero) and allow for independent adjustment of the diffusion weighting, b, and the velocity dispersion weighting, α.

FIG. 4 displays schematics of pulse sequences for motion weighted nuclear magnetic resonance (NMR) or magnetic resonance imaging (MRI). The magnification of the motion encoding block shows the effective gradient wave form for four commonly known motion encoding schemes: 1. single-PGSE, non-compensated (signal attenuation from diffusion and perfusion); 2. double-PGSE, non-compensated (signal attenuation from diffusion and perfusion); 3. double-PGSE, flow-compensated (signal attenuation from diffusion but NOT from perfusion). 4. n-PGSE, flow-compensated (signal attenuation from diffusion but NOT from perfusion). Each gradient pulse pair is characterized by its amplitude G, pulse duration δ, and separation between leading edges Δ.

FIG. 5 shows simulated MR signal vs. diffusion-weighting b for some of the pulse sequences in FIG. 4. The simulations were based on the following parameters estimated on invasive ductal carcinoma by Sigmund et al. (2): perfusion fraction f=10.5%, tissue diffusivity D=1.14 μm²/ms, pseudo-diffusivity of the perfusion fraction D*=14.9 μm²/ms.

(a) Data obtained with a conventional protocol (obtained from ref. (2)) using a non-compensated single PGSE motion encoding scheme yielding signal attenuation from diffusion and perfusion. Circles: simulated noisy data; solid line: result of a conventional least squares fit yielding estimates of the perfusion fraction f, pseudo-diffusivity of the perfusion fraction D*, and tissue diffusivity D; dashed line: signal attenuation of the diffusion fraction. The perfusion fraction equals the difference between the b=0 intercepts of the solid and dashed lines.

(b) Data obtained with a protocol according to the present invention in which results from non-compensated single PGSE and flow-compensated double PGSE protocols are analyzed simultaneously. Circles: simulated noisy non-compensated data; squares: simulated noisy flow-compensated data; solid and dash-dotted lines: result of a simultaneous least squares fit to the non-compensated and flow-compensated according to the present invention yielding estimates of the perfusion fraction f, $v_d^2$ for the perfusion fraction, and diffusivity of the diffusion fraction D; dashed line: signal attenuation of the diffusion fraction. The perfusion fraction equals the difference between the dashed and dash-dotted lines.

Figure 6:
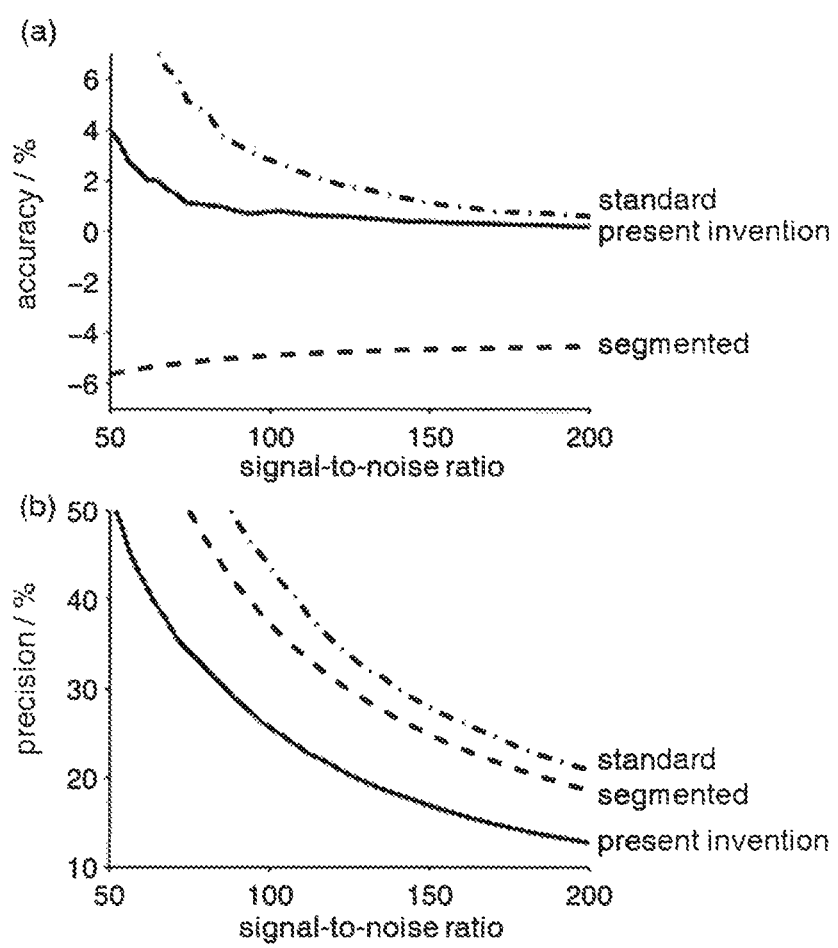
FIG. 6 shows the accuracy and the precision of the perfusion fraction f as quantified with conventional protocols ("standard" and "segmented"), as well as according to the present invention.

FIG. 6 shows the accuracy (a) and the precision (b) of the perfusion fraction f as quantified with conventional protocols ("standard" and "segmented") as well as according to the present invention. The accuracy and precision are plotted as a function of the signal-to-noise ratio of the raw MR signal data. Note the better accuracy and precision of the present invention when compared with the conventional protocols over the whole range of signal-to-noise ratios.

REFERENCES

1. Le Bihan D, et al. (1988) Separation of diffusion and perfusion in intravoxel Incoherent motion MR imaging. *Radiology* 168:497-505.
2. Sigmund E E, et al. (2011) Intravoxel Incoherent Motion Imaging of Tumor Microenvironment in Locally Advanced Breast Cancer. *Magn. Reson. Med.* 65:1437-1447.
3. Luciani A, et al. (2008) Liver Cirrhosis: Intravoxel Incoherent Motion M R Imaging—Pilot Study. *Radiology* 249:891-899.
4. Lemke A, Laun F B, Simon D, Stieltjes B, & Schad L R (2010) An In Vivo Verification of the Intravoxel Incoherent Motion Effect in Diffusion-Weighted Imaging of the Abdomen. *Magn. Reson. Med.* 64:1580-1585.
5. Provencher S W (1982) A constrained regularization method for inverting data represented by linear algebraic or integral equations. *Computer Phys. Comm.* 27:213-227.

6. Ahn C B, Lee S Y, Nalcioglu O, & Cho Z H (1987) The effects of random directional distributed flow in nuclear magnetic resonance imaging. *Med. Phys* 14:43-48.
7. Maki J H, MacFall J R, & Johnson G A (1991) The use of gradient flow compensation to separate diffusion and microvasculatory flow in MRI. *Magn. Reson. Med.* 17:95-107.
8. Callaghan P T, Codd S L, & Seymour J D (1999) Spatial coherence phenomena arising from translational spin motion in gradient spin echo experiments. *Conc. Magn. Reson.* 11(4):181-202.
9. Wang Z, Su M-Y, & Nalcioglu O (1998) Measurement of Tumor Vascular Volume and Mean Microvascular Random Flow Velocity Magnitude by Dynamic Gd-DTPA-Albumin Enhanced and Diffusion-Weighted MRI. *Magn. Reson. Med* 40:397-404.
10. Le Bihan D & Turner R (1992) The Capillary Networkl A Link between IVIM and Classical Perfusion. *Magn. Reson. Med.* 27:171-178.
11. Kim T & Kim S-G (2006) Quantification of Cerebral Arterial Blood Volume Using Arterial Spin Labeling With Intravoxel Incoherent Motion-Sensitive Gradients. *Magn. Reson. Med.* 55:1047-1057.
12. Hunter M W, Jackson A N, & Callaghan P T (2010) PGSE NMR measurement of the non-local dispersion tensor for flow in porous media. *J. Magn. Reson.* 204:11-20.
13. Le Bihan D, Turner R, Moonen C T W, & Pekar J (1991) Imaging of Diffusion and Microcirculation with Gradient Sensitization: Design, Strategy, and Significance. *J. Magn. Reson. Imaging* 1:7-28.
14. van Kampen N G (1981) *Stochastic Processes in Physics and Chemistry* (North-Holland, Amsterdam).
15. Alper J S & Gelb R I (1990) Standard errors and confidence intervals in nonlinear regression: Comparison of Monte Carlo and parametric statistics. *J. Phys. Chem.* 94:4747-4751.

The invention claimed is:

1. A method for magnetic resonance (MR) imaging, comprising:
 performing magnetic resonance (MRI imaging on a sample, wherein the performing the MR imaging includes
  generating radio frequency (RF) and magnetic gradient pulse sequences,
  acquiring at least two MR images with different motion-weighting originating from a RF and gradient pulse sequence causing signal attenuation from diffusion as first data, based on measuring signals received from the sample based on the generated RF and magnetic gradient pulse sequences, and
  acquiring at least two MR images with different motion-weighting originating from a RF and gradient pulse sequence causing signal attenuation from diffusion as second data, based on measuring signals received from the sample based on the generated RF and magnetic gradient pulse sequences,
  wherein the first data and the second data are data sets acquired with different degrees of flow compensation:
 performing a model fit to each set of data of the first data and the second data in which at least one parameter of a plurality of adjustable parameters are constrained to be common for both sets of data of the first data and the second data; and obtaining quantitative information on microscopic flow based on extracting at least one parameter of an intravoxel incoherent motion (MM) effect from the model fit.

2. The method according to claim 1, wherein effects of diffusion and perfusion on a pseudo-diffusion coefficient, D*, are analyzed separately based on the first data and the second data.

3. The method according to claim 1, wherein diffusion weighting, b, and velocity dispersion weighting, α are adjusted independently of each other to perform a diffusion-perfusion correlation experiment.

4. The method according to claim 3, wherein diffusion weighting, b, and velocity dispersion weighting, α, are adjusted independently of each other to quantify the velocity dispersion by disentangling diffusion contributions and velocity dispersion contributions to a total signal attenuation.

5. The method according to claim 1, wherein a measurement of a correlation between diffusion coefficient and velocity dispersion allows associating velocity dispersion components and corresponding diffusion components when one or more diffusion or velocity dispersion components are present.

6. The method according to claim 1, wherein diffusion coefficients D and $D_f$, velocity dispersion $v_d^2$, ratio f and intensity $I_0$ can be quantified by regressing an equation $$I(b, \alpha) = I_0 \left[ f e^{-bD_f} e^{-\alpha^2 v_d^2} + (1-f) e^{-bD} \right]$$

onto the signal attenuation data I(b,α).

7. The method according to claim 1, wherein
 the first data is flow-compensated data, and
 the flow-compensated data is recorded with a n-PGSE or oscillating gradient sequence to minimize the signal attenuation due to flow.

8. The method according to claim 1, wherein
 the second data is non-flow compensated data, and
 the non-flow compensated data is recorded with a single-PGSE with $\Delta_s \gg \delta_s$ to maximize the signal attenuation due to flow for a given echo time, where $\delta_s$ is a pulse duration and $\Delta_s$ is a leading edge pulse separation.

9. The method according to claim 1, wherein image intensities are analyzed by regressing $$I(q_n, \Delta_n, \delta_n) = I_{0n} \left[ (1-f) e^{-nq_n^2(\Delta_n - \delta_n/3)D} + f e^{-nq_n^2(\Delta_n - \delta_n/3)D_f} \right]$$

to repeated flow-compensated doubled pulsed gradient spin-echo, n-PGSE, data and $$I_s(q_s, \Delta_s, \delta_s) = I_{0s} \left[ (1-f) e^{-q_s^2(\Delta_s - \delta_s/3)D} + f e^{-q_s^2(\Delta_s - \delta_s/3)D_f} e^{-q_s^2 \Delta_s^2 v_d^2} \right]$$

to non-compensated single pulsed gradient spin-echo, single-PGSE, data under the constraint that D, $D_f$ and f are the same for both sets of data,
 wherein $q_n$, $\Delta_n$ and $\delta_n$ denote a dephasing magnitude, a leading edge pulse separation and a pulse duration, respectively, for a double-PGSE sequence, wherein $q_s$, $\Delta_s$ and $\delta_s$ denote a dephasing magnitude, a leading edge pulse separation and a pulse duration, respectively, for a single-PGSE sequence, and wherein f is a perfusion factor.

10. The method according to claim 1, wherein image intensities are analyzed by regressing $$I(q_n, \Delta_n, \delta_n) = I_0 e^{-nq_n^2(\Delta_n - \delta_n/3)D}$$

to repeated flow-compensated doubled pulsed gradient spin-echo, n-PGSE, data and $$I_s(q_s, \Delta_s, \delta_s) = I_{0s}\left[(1-f)e^{-q_s^2(\Delta_s - \delta_s/3)D} + fe^{-q_s^2(\Delta_s - \delta_s/3)D_f}e^{-q_s^2\Delta_s^2 v_d^2}\right]$$

to non-compensated single pulsed gradient spin-echo, single-PGSE, data under a constraint that D and/or $I_0$ are the same for both sets of data wherein $q_n$, $\Delta_n$ and $\delta_n$ denote a dephasing magnitude, a leading edge pulse separation and a pulse duration, respectively, for a double-PGSE sequence, wherein $q_s$, $\Delta_s$ and $\delta_s$ denote a dephasing magnitude, a leading edge pulse separation and a pulse duration, respectively, for a single-PGSE sequence, and wherein f is a perfusion factor.

11. The method according to claim 6, wherein anyone of $v_d^2$, $\sqrt{v_d^2}D$, $D_f$, and f are used for generating MR image contrast.

12. The method according to claim 1, wherein the quantitative information is related to tumor vascular properties.

13. The method according to claim 12, wherein the tumor vascular properties are blood volume fraction and/or microvascular flow velocity.

14. The method according to claim 1, wherein the quantitative information consists of at least parameters CBV (cerebral blood volume) and/or CBF (cerebral blood flow).

* * * * *